United States Patent
Siebers et al.

(10) Patent No.: US 9,295,781 B2
(45) Date of Patent: Mar. 29, 2016

(54) BOROSILICATE GLASS SYRINGE WITH CONE COATING THAT INCREASES SURFACE ROUGHNESS

(71) Applicant: SCHOTT AG, Mainz (DE)

(72) Inventors: Friedrich Siebers, Nierstein (DE); Inka Henze, Nieder-Olm (DE); Juergen Thuerk, St. Gallen (CH)

(73) Assignee: SCHOTT AG, Mainz (DE)

( * ) Notice: Subject to any disclaimer, the term of this patent is extended or adjusted under 35 U.S.C. 154(b) by 569 days.

(21) Appl. No.: 13/718,226

(22) Filed: Dec. 18, 2012

(65) Prior Publication Data

US 2013/0158485 A1    Jun. 20, 2013

(30) Foreign Application Priority Data

Dec. 19, 2011    (DE) .......................... 10 2011 089 045

(51) Int. Cl.
*A61M 5/31* (2006.01)
*A61M 5/34* (2006.01)

(52) U.S. Cl.
CPC ............... *A61M 5/31* (2013.01); *A61M 5/3129* (2013.01); *A61M 5/3134* (2013.01); *A61M 5/346* (2013.01); *Y10T 428/139* (2015.01); *Y10T 428/1393* (2015.01)

(58) Field of Classification Search
CPC .. A61M 5/3134; A61M 5/31; Y10T 428/139; Y10T 428/1393
USPC ............................................... 428/36.9, 36.91
See application file for complete search history.

(56) References Cited

U.S. PATENT DOCUMENTS

| 4,589,871 A | 5/1986 | Imbert |
| 5,203,902 A | 4/1993 | Murkens |
| 5,851,201 A | 12/1998 | Ritger et al. |
| 6,043,171 A | 3/2000 | Siebers et al. |
| 2006/0189470 A1 | 8/2006 | Mitra |

FOREIGN PATENT DOCUMENTS

| CN | 1042890 A | 6/1990 |
| CN | 1810693 | 8/2006 |
| DE | 19512847 C1 | 11/1996 |
| DE | 19721737 C1 | 11/1998 |
| DE | 19834801 A1 | 2/2000 |
| EP | 0370683 A1 | 5/1990 |
| EP | 0558942 A1 | 9/1993 |
| EP | 0585830 A1 | 3/1994 |
| EP | 1683767 A1 | 7/2006 |
| WO | 2010150042 A1 | 12/2010 |

OTHER PUBLICATIONS

Search Report of the European Patent Office dated Jul. 14, 2014 for corresponding European Patent Application No. 12193370.9, 10 pages.

*Primary Examiner* — Walter B Aughenbaugh
(74) *Attorney, Agent, or Firm* — Ohlandt, Greeley, Ruggiero & Perle, LLP

(57) ABSTRACT

A syringe made of borosilicate glass and having a cone for fastening or mounting of transfer adapters and needles is provided. The cone includes a coating that increases roughness. The coating has structure-forming particles are embedded in a glass matrix and is free of Pb, Cd, Hg and $Cr^{VI}$.

22 Claims, 1 Drawing Sheet

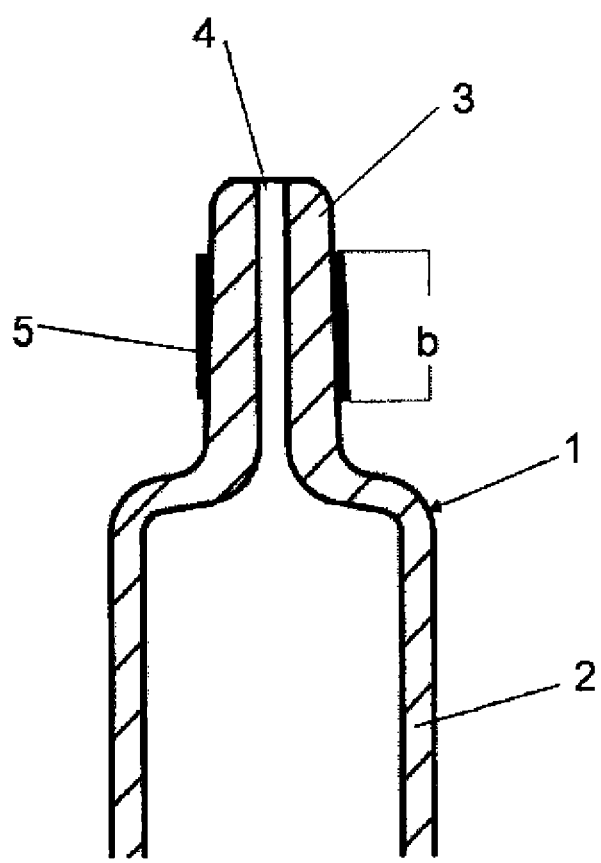

BOROSILICATE GLASS SYRINGE WITH CONE COATING THAT INCREASES SURFACE ROUGHNESS

CROSS REFERENCE TO RELATED APPLICATIONS

This application claims benefit under 35 U.S.C. §119(a) of German Patent Application No. 10 2011 089 045.0 filed Dec. 19, 2011, the entire contents of which are incorporated herein by reference.

BACKGROUND OF THE INVENTION

1. Field of the Invention

The present invention relates to a syringe which is composed of borosilicate glass and has a coating of the syringe cone for setting a defined surface roughness. Such a coating is applied in the form of a ceramic ink to the cone and baked. The ink composition used for this purpose consists of a glass frit, a roughness additive and liquid organic constituents which volatilize or decompose during baking. The glass frit melts and flows during baking, while the roughness additive does not melt during baking of the layer and essentially retains its shape and represents embedded, structure-forming particles in the molten glass layer which are raised on the surface of the layer. The glass matrix of the molten layer in which the structure-forming particles are embedded is also referred to as glass flux.

2. Description of Related Art

It is known that inorganic inks can be used for coating, also referred to as decoration or printing, of glass articles. Such inks contain one or more glass frits and optionally one or more color-coating components (pigments) in amounts of usually about 20% by weight. The glass frit is produced by melting and subsequent quenching and comminution of a glass composition. The glass frit obtained is milled to particle sizes of preferably less than 30 micrometers (μm) and mixed with the pigment powders.

Depending on the coating technique used, the powder constituents are mixed with specific organic suspension media, e.g. screen printing oil, to form a paste and applied to the glass substrate to be coated. The organic suspension medium has to burn out without leaving a residue before sintering and flowing and leveling of the glass powder because otherwise bubble formation occurs in the coating and the latter displays reduced adhesion to the substrate. The properties of the organic components play a part in determining the method of application, the reproducibility and the stability of the pastes in the application process. Critical parameters are the evaporation and drying behavior, the viscosity and the pasting ratio, i.e. the ratio of solid to liquid constituents or of organic component to inorganic powder. These parameters determine, inter alia, the layer thicknesses which can be achieved in the application process, when using the screen printing technique, the operating time of screens or of other printing elements and also the storage times of made-up inks in stock vessels.

In the baking process, the glass particles of the frit soften, flow and level out, envelop the color pigments and ensure, by means of diffusion processes, adhesion of the baked layer on the glass substrate. The glass particles of the frit are therefore essentially responsible for the chemical and physical properties of the decoration or ink layer after baking. The baking of the ink has to take place at below the deformation temperature of the glass substrate so as to avoid uncontrolled deformation of the substrate which has been printed, coated or decorated. For this reason, it is necessary to use low-melting glass frits which can be baked at below 700 degrees Celsius (° C.), especially for the decoration of, for example, borosilicate glasses having transformation temperatures of about 560° C.

The glass frits used hitherto for coating borosilicate glasses usually have a high lead content which is added in order to lower the baking temperature. Apart from the low baking temperatures, lead-containing glass frits have further technical advantages. They allow coating of borosilicate glasses having a low thermal expansion of from about 3 to $6 \cdot 10^{-6}$/K without adhesion problems occurring. Furthermore, lead-containing glass frits make it possible to provide coatings having good chemical resistance towards acids and bases. This is an advantage for many applications of borosilicate glasses since these are frequently used because of their good chemical resistance.

Despite these good technical properties, the production and processing of lead containing glass frits is problematical, including during melting and milling. The toxic properties of lead-containing glass frits require special treatment in respect of handling, processing and disposal of the products decorated therewith. Due to new and stricter directives which limit the use of lead in glass frits, there is an increasing need for lead-free glass frits.

Commercially available lead-free inks for baking temperatures of about 650° C. have thermal expansions of greater than $6 \cdot 10^{-6}$/K and therefore tend to be suitable for coating soda-lime glass having a thermal expansion of from about 8 to $9 \cdot 10^{-6}$/K. The thermal expansion of such ink coatings is therefore not sufficiently matched to borosilicate glasses, and damage such as cracks, spalling and damage to the substrate glass can easily occur in the coated regions.

One possible way of reducing stresses between a coating and a borosilicate glass substrate is application of very thin layers, but this has the disadvantage of reduced color intensity. The chemical resistance of lead-free inks is also unsatisfactory for many applications.

The requirements which a coating of a cone of glass syringes has to meet are different from those for otherwise customary coatings for, for example, decorative purposes. To obtain color coatings having a good color intensity, layer thicknesses of greater than 20 μm are generally desired. The layer thickness of cone coatings, on the other hand, should ensure functionality and preferably be visible for the purposes of quality monitoring, but can be thinner. While conventional, decorative color coatings have to be smooth for aesthetic reasons and also to allow easier cleaning, the cone coating has to have a defined roughness. This defined roughness ensures that adapters placed on the cone of a syringe for the transfer of a liquid medicament present in the syringe cylinder stick firmly to the syringe or the cone thereof. These adapters are usually plastic adapters having a standardized geometry and having injection needles or tubing for the transport of the liquid attached thereto. The improved adhesion of the adapter to the cone associated with the defined roughness ensures that an adapter does not become detached by the internal pressure or lateral forces occurring during injection. A syringe adapter placed on the cone should also stick sufficiently well for it to remain firmly joined to the syringe body when pulling out the needle after injection. On the other hand, the roughness must not be too great because then there is the risk of an unsatisfactory seal. An unsatisfactory seal can lead to part of the medical liquid being expressed between adapter and syringe cone by the pressure required during injection and being lost, resulting in the surroundings being contaminated by the expressed droplets. Furthermore, prefilled ready-made syringes containing medical liquid are sealed with closure caps on the cone after filling and stored. During this storage, a good seal is important so that the medical liquid is stored safely and sealed hermetically from the surroundings and atmosphere.

Pharmaceutical packaging is subject to more demanding requirements in respect of safety, toxic pollution and environmental friendliness. Thus, the EU directive EU 94/62/EC and also the packaging regulations Coneg applicable in the United States of America requires the total content of the elements Pb, Cd, Hg and $Cr^{VI}$ to be limited to less than 100 parts per million (ppm) (corresponds to 0.01% by weight) per article. This limit value is easily exceeded when using cone coatings based on lead-containing glass frits, particularly in the case of small and light glass syringes.

Good adhesion of the coating without cracks, spalling of the coating and reductions in strength of the glass substrate occurring is therefore particularly important for the desired function of cone coatings. This requires matching of the thermal expansion of the cone coating to the type of glass of which the syringe is made. Stresses due to differences in the thermal expansion have to be minimized so that the above-mentioned types of damage are avoided.

It is also desirable to have a good chemical resistance of the cone coating so that cleaning operations, e.g. autoclaving or washing of the glass syringe with usually acid or basic cleaning agents, do not attack the cone coating. The set roughness of the coating surface is also not intended to be altered by chemical attack.

To ensure that the glass body of a syringe composed of borosilicate glass does not deform during baking, the glass frit in the color also has to have a low baking temperature of less than 700° C.

Cone coatings for syringes are described in U.S. Pat. No. 4,589,871 A. The syringe bodies can consist of metal, plastic, glass and ceramic. Roughness additives described are powders of ceramic, glass, metal or combinations thereof to which an oil is added. This suspension is printed onto the syringe cone and the liquid constituents are partly vaporized in an oven, while the particles should remain adhering to the cone surface. However, no information is given for the cone coating of syringes of the borosilicate glass type with their low thermal expansion. There is also no information given as to the required nature of the roughness additive. Furthermore, it can be expected that the adhesion force of the applied particles to the cone leaves something to be desired. In addition, no roughness values are given for optimal functioning of the coating.

U.S. Pat. No. 5,851,201 A describes a syringe which is provided on the outside in the cone region with a textured surface for defined setting of the adhesion forces. The roughness is generated by embossing the texture into the surface of the syringe cone.

As an alternative to application of a coating having a defined roughness, the glass syringe can also be roughened in the cone region by means of grinding tools or sandblasting. However, it is difficult or complicated to provide a defined roughness in this way. In addition, these processes produce, especially in the case of syringes, very undesirable contamination due to abrasion and particles and make complicated cleaning steps necessary.

SUMMARY

It is an object of the invention to provide a glass syringe which is composed of borosilicate glass and has a cone coating which can be closed with sufficient sealing effect and can reliably hold adapters placed on the cone thereof. The adhesion of fitted adapters should be increased and, secondly, a reliable seal should be ensured. In addition, the syringes should be able to be produced economically and meet the requirements of the regulations governing the pharmaceuticals industry.

Since borosilicate glasses have particularly good chemical resistance and are therefore largely inert towards a medical liquid even during prolonged storage times, the cone coating should be directed at syringes made of this type of glass. The FIOLAX® borosilicate glass from SCHOTT AG, Germany, formerly from SCHOTT-Rohrglas GmbH, is a standard for pharmaceutical packaging and has depending from the type a thermal expansion in the temperature range from 20 to 300° C. of 4.9 to $5.5 \cdot 10^{-6}$/K. The cone coating should, inter alia, be suitable for this borosilicate glasses.

These objects are achieved by a syringe having a cone coating.

The glass syringe should consist of a borosilicate glass. Borosilicate glass has a high chemical resistance, can be sterilized readily and has excellent barrier properties against oxygen in order to protect the liquid medicament. Owing to its low alkali content, it is largely inert towards the medicament, even in the case of prolonged storage and contact times. The thermal expansion of the borosilicate glass is dependent first and foremost on the alkali contents. To achieve inert behaviour and good processing properties in hot forming by means of flame burners, the borosilicate glass of the syringe should have a thermal expansion in the range from 20 to 300° C. of less than $6 \cdot 10^{-6}$/K, preferably not more than $5.5 \cdot 10^{-6}$/K and especially preferred less than $5 \cdot 10^{-6}$/K. In the case of high demands made of pharmaceutical packaging, it is therefore advantageous to use a borosilicate glass such as the proven FIOLAX® from SCHOTT AG. This has a low thermal expansion in the temperature range from 20 to 300° C. of 4.9 to $5.5 \cdot 10^{-6}$/K, depending from the type. The transformation temperature of this glass is, as is typical of borosilicate glasses, 565° C. In order to rule out deformation of a glass syringe composed of this type of glass, baking of the cone coating is carried out at below 700° C. and preferably below 660° C. For the flowing and leveling of the cone coating and secure adhesion to the syringe cone, the coating contains 70-99% by weight of a low-melting glass matrix which achieves a viscosity of greater than or equal to $10^6$ dPas at a temperature below 700° C. This viscosity value ensures, at average particle sizes of the glass frit of about 3 urn, the flow and leveling of the glass powders during firing and the production of a layer which adheres well to the substrate. This viscosity is preferably achieved even below 660° C. during baking, since when using particularly finely milled glass powders, the baking temperatures can be reduced to below 660° C.

To ensure the function of secure adhesion and sealing of adapters and closure caps placed on the cone, the cone coating comprises, in addition to the glass frit, from 1 to 30% by weight of a pulverulent roughness additive. Preference is given to a content of from 4 to 25% by weight. While the glass frit is responsible for the flow and levelling and the adhesion of the cone coating to the glass substrate, a defined roughness is set via the additive added. The particles of the additive should themselves not flow and become level on baking, but should instead retain their original shape.

The cone coating is, within the usual technical limits, free of the problematical elements Pb, Cd, Hg and $Cr^{VI}$. This means that components containing these elements are not deliberately added as constituent to the coating or the starting color and these elements are merely introduced as impurities which are unavoidable within a justifiable outlay. Based on the entire syringe, the total concentration of these elements due to impurities is below 1000 ppm, preferably below 100 ppm.

To ensure an optimal function, the roughness value of the cone coating is set to values of $R_q$(rms)=0.3 to 2 µm and preferably from 0.5 to 1.8 µm. Here, the $R_q$(rms) value (rms: root mean square) corresponds to the mean of the height deviations z(x) measured from the average height surface in the measurement range and is determined according to the formula given below.

$$R_q = \sqrt{\frac{1}{L}\int_0^L z^2(x)dx}$$

Here, x is the lateral location coordinate along the measurement section from 0 to L.

The roughness corresponds to the adhesion of the adapter. Particularly advantageous values for the adhesion and sealing are achieved at values of $R_q$(rms)=0.5 to 1.8 µm. These values achieve a good compromise between adhesion and sealing.

For the function of the cone coating in respect of adhesion and sealing, it is advantageous for the average layer thickness to be from 0.5 to 20 µm. At layer thicknesses of about 0.5 µm, it is observed, inter alia, that the cone coating does not completely cover the syringe cone everywhere. Within coated areas, there are then island-like subregions which are free of coating. It has been found that a coating which is incomplete only in places is not critical for the function. However, below an average layer thickness of 0.5 µm the cone coating becomes visually inconspicuous. This means that differences in the layer thickness can barely be observed in visual quality control. The possible deviations in respect of the adhesion forces therefore also increase. The average layer thickness of the cone coating should therefore be at least 0.5 µm. At an average layer thickness of the cone coating above 20 µm the mechanical stresses between the coating and the glass syringe composed of borosilicate glass are increased, which can lead to cracks or spalling. The strength of the glass syringe in the cone region can be lowered in an unacceptable way by this damage. Average layer thicknesses of from 2 to 15 µm are particularly advantageous because layers having this thickness are readily visible and the mechanical stresses are reduced.

The roughness of the cone coating depends, in particular, on the type, amount and particle size distribution of the roughness additives used. The average particle size $d_{50}$ of the roughness additive is advantageously set to values of from 0.2 to 5 µm. The choice of particle size depends on the layer thickness of the cone coating set in the application process. At relatively great layer thicknesses, it is advantageous in terms of producing the desired roughness value for the particle size to be selected in the upper region of the range indicated. This is because at greater layer thicknesses the grains or particles of the additive are enclosed to a greater extent by the glass flux. A decisive aspect for the selection of the particle size of the additive is achievement of the desired roughness values. After flowing and leveling of the coating applied to the cone during baking, the particles of the roughness additive partly project from the glass matrix formed by the glass flux and thereby form a rough surface structure. The particles of the roughness additive are therefore also referred to as structure-forming particles.

Various types of roughness additives are possible. It is possible to use ceramic powders such as α-alumina, zirconium silicate, barite, $TiO_2$, $ZrO_2$. It is likewise possible to add a hard glass, e.g. fused silica or another glass having a melting point which is significantly higher than that of the glass frit and having a higher viscosity as pulverulent roughness additive. It is advantageous to add an additive whose thermal expansion is not greater than the thermal expansion of the glass flux used. In this way, the thermal expansion of the resulting total coating can be reduced by the addition of the additive. This results in better matching of the thermal expansion to the substrate which consists of low-expansion borosilicate glass. It is advantageous for the thermal expansion of the roughness additive in the temperature range from 20 to 300° C. to be less than $8 \cdot 10^{-6}$/K and particularly advantageously less than $5 \cdot 10^{-6}$/K. Such advantageous additives consist, for example, of cordierite, fused silica, eucryptite, zirconium silicate and mullite.

Suitable glass frits for coating borosilicate glasses having a low coefficient of thermal expansion have a thermal expansion in the range from 20 to 300° C. of less than $7.5 \cdot 10^{-6}$/K and preferably less than $7 \cdot 10^{-6}$/K. These glass fluxes make firmly adhering coatings up to a layer thickness of about 20 µm possible without cracks and spalling occurring, which would be very undesirable for the intended use in the pharmaceutical sector. The thermal expansion should be greater than $4 \cdot 10^{-6}$/K for matching to the glass substrate.

To achieve good flow and leveling and adhesion of the coating to the borosilicate glass, the particle size of the glass frit should be very fine. To prevent the technical outlay in fine milling from being too great, milling is carried out to an average particle size of from about 1 to 5 µm. The average particle size of the glass powders is preferably from about 2 to 4 µm.

The requirements which the glass frit has to meet, e.g. environmentally friendly composition, matching to the glass syringe consisting of borosilicate glass in respect of baking temperature and matching of the coefficient of thermal expansion, are advantageously satisfied by two glass systems.

The use of the crystallographically related and toxicologically unproblematic Bi as replacement for Pb leads to the $Bi_2O_3$-$B_2O_3$-$SiO_2$ glass system. This glass system contains, as main constituents, 40 to 75% by weight of $Bi_2O_3$, 3 to 20% by weight of $B_2O_3$ and 10 to 30% by weight of $SiO_2$, which form the glass framework. Minimum contents of 40% by weight of $Bi_2O_3$, 10% by weight of $SiO_2$ and 3% by weight of $B_2O_3$ are necessary for this. $Bi_2O_3$ contents above 75% by weight lead to an unacceptable increase in the thermal expansion. $B_2O_3$ contents above 20% by weight are disadvantageous in respect of the chemical resistance. $SiO_2$ is present in amounts of not more than 30% by weight. Higher contents would increase the baking temperature above the limits with regard to deformation of glass syringes composed of borosilicate glass.

It is particularly advantageous for the glass frit to comprise essentially the following components (in % by weight on an oxide basis) or consist thereof:

$Bi_2O_3$ 55 to 70% by weight;
$B_2O_3$ 5 to 15% by weight;
$SiO_2$ 15 to 30% by weight;
$\Sigma\ Li_2O+Na_2O+K_2O$ 1 to 5% by weight;
$\Sigma\ MgO+CaO+SrO+BaO$ 0 to 4% by weight;
ZnO 0 to 4% by weight;
$Al_2O_3$ 0 to 5% by weight; and
$\Sigma\ TiO_2+ZrO_2$ 0 to 5% by weight.

This composition achieves a further improvement in meeting the demands made of the cone coating in respect of low thermal expansion, matched to borosilicate glass, and a low baking temperature. The contents of alkalis and alkaline earths reduce the viscosity and thus the baking temperature, but must not be too high because otherwise the thermal expansion of the glass flux component or the glass matrix in the coating is unacceptably increased. The additions of $Al_2O_3$, $TiO_2$ and $ZrO_2$ improve the glass stability and counter undesirable crystallization. However, contents higher than those indicated lead to an increase in the viscosity and the baking temperature. The content of ZnO is limited because this component can otherwise lead to undesirable crystallization.

An alternative, second glass system which can meet the demands made of the glass frit is the $ZnO$—$B_2O_3$-$SiO_2$ glass system. These three components as main constituents form the glass framework. These main constituents are present in proportions of 15 to 48% by weight of ZnO, 8 to 40% by weight of $B_2O_3$ and 8 to 52% by weight of $SiO_2$. This glass system makes it possible to obtain comparatively low coefficients of thermal expansion of about $6 \cdot 10^{-6}$/K in the range from 20 to 300° C.

At $SiO_2$ contents above 52% by weight, the chemical resistance improves further but the viscosity and the baking temperature increase unacceptably. A disadvantage of low $SiO_2$ contents below 8% by weight is the reduced chemical resistance to acids and bases, so that here it is always important to find a compromise composition which meets requirements.

The minimum content of ZnO should be 15% by weight and the minimum content of $B_2O_3$ should be 8% by weight. This is necessary because otherwise the baking temperatures would increase too much. Contents higher than 48% by weight of ZnO and 40% by weight of $B_2O_3$ are disadvantageous in respect of the chemical resistance and lead to glass frits which during baking are very susceptible to undesirable crystallization.

Crystallization of the glass frit is undesirable because this crystallization progresses from the surfaces and the crystal layer which forms prevents sintering and flow and leveling of the glass powder. Crystallization-susceptible glass frits therefore usually lead to porous layers which do not adhere well and can easily be removed by mechanical means. Since the crystallization cannot be readily controlled because of its strong temperature dependence and particle size dependence, it is less suitable for setting a defined roughness.

A particularly advantageous composition of the glass frit comprises essentially the following components (in % by weight on an oxide basis) or consists thereof:

ZnO 17 to 35% by weight;
$B_2O_3$ 10 to 30% by weight;
$SiO_2$ 20 to 50% by weight;
$\Sigma Li_2O + Na_2O + K_2O$ 1 to 15% by weight;
$\Sigma MgO + CaO + SrO + BaO$ 0 to 3% by weight;
$Al_2O_3$ 0 to 3% by weight; and
$\Sigma TiO_2 + ZrO_2$ 0 to 7% by weight.

This composition achieves a further improvement in the desired properties in respect of low thermal expansion matched to borosilicate glass and low baking temperature. The contents of alkalis reduce the viscosity and thus the baking temperature but must not be higher because otherwise the thermal expansion of the glass frit increases unacceptably. The additions of alkaline earths and $Al_2O_3$, $TiO_2$ and $ZrO_2$ improve the glass stability and counter undesirable crystallization. Contents higher than those indicated lead to an undesirable increase in the viscosity and the baking temperature.

A further object of the invention is to provide a glass syringe composed of borosilicate glass and having an environmentally friendly cone coating which ensures satisfactory adhesion and freedom from leaks of attached adapters and closure caps. In terms of the function of the glass syringe, it has been found to be advantageous for the cone coating to be rotationally symmetrical around the cone and have a width of from 2 to 10 mm. This width is advantageous for conventional closure caps and adapters. Smaller widths can lead to undesirable deviations in terms of sealing and adhesion. The width of the coating is limited to a maximum of 10 mm by the size of the syringe cone of conventional glass syringes. Greater widths lead to a more difficult coating process. The circumferential coating is applied in an application process, for example by means of pressure rollers or pressure bands, with the glass syringe being rotated during the printing operation in order to ensure a uniform layer thickness. The cone coating is advantageously circumferential without interruption so that sealing problems do not occur. To allow visual quality control, the coating should preferably be visible with the naked eye. It can be transparent to translucent, which is generally ensured by the sintering process and the differences in refractive index between glass frit and roughness additive and also the roughness of the cone coating.

To increase visibility up to 5% by weight of a white pigment, e.g. $TiO_2$, can be added to the glass frit in addition to the roughness additive. A syringe which has been coated according to the invention thus does not ensure the functions of the syringe but measures for quality monitoring during production are also made possible by the geometry and appearance of the coating.

The coated glass syringe contains, based on its total weight, a total of less than 100 ppm of the toxicologically problematical elements Pb, Cd, Hg, $Cr^{VI}$ and thus meets the legal requirements for pharmaceutical packaging. The coating of the glass syringe consists of a low-melting glass having a viscosity of less than or equal to $10^6$ dPas below 700° C. and 1 to 30% by weight of a roughness additive. At this viscosity value which is to be achieved for sintering and flow and leveling, the required low baking temperatures are ensured. It is advantageous for this viscosity value to be achieved even below 660° C. because the baking temperature can then be reduced further. The proportion of from 1 to 30% by weight of the roughness additive ensures the defined roughness.

Further properties of the cone coating present on the glass syringe are selected according to what has been said above. Thus, an average layer thickness of the cone coating of from 0.5 to 20 μm and an average particle size $d_{50}$ of the roughness additives as structure-forming particles of from 0.2 to 5 μm are advantageous. Furthermore, a low thermal expansion of the roughness additives is advantageous, as is a thermal expansion of the glass flux component or of the glass matrix of the coating of less than $7.5 \cdot 10^{-6}$/K and preferably less than $7 \cdot 10^{-6}$/K in the temperature range from 20 to 300° C.

The glass syringe consists of a borosilicate glass which is particularly inert towards the liquid medicaments. Since this requires low alkali contents of the borosilicate glass, it is associated with a low thermal expansion of less than $6 \cdot 10^{-6}$/K, preferably not more than $5.5 \cdot 10^{-6}$/K and more preferred less than $5 \cdot 10^{-6}$/K. Although this increases the demands made of the matching of the thermal expansion of the cone coating, it is a great advantage for inert behavior since only very few alkali metal ions go into solution even on prolonged storage. Below a thermal expansion of the borosilicate glass of $4.5 \cdot 10^{-6}$/K, matching of the thermal expansion of the cone coating becomes more difficult and stresses and cracks or adhesion problems of the cone coating occur.

BRIEF DESCRIPTION OF THE DRAWINGS

The sole FIGURE shows a front section of a glass syringe according to the present disclosure.

DETAILED DESCRIPTION OF THE INVENTION

The sole FIGURE shows the front section of a glass syringe 1 with cylinder 2, cone 3, outlet channel 4 and circumferential cone coating in longitudinal section. A typical dimension of the circumferential cone coating would be a width b of 5 mm. If the coating 5 is, as shown, arranged in the central, middle region of the glass cone, this is particularly advantageous for the function and handling when attaching adapters and sealing caps.

In the case of this configuration of the cone coating, deviations in the roughness, e.g. as a result of fluctuating baking temperatures or layer thicknesses, are very readily visible under appropriate lighting conditions and can be utilized for the final quality control of the coated syringes.

The present invention is illustrated by the following examples.

The glass compositions for the glass frits of Table 1 were melted from conventional industrial mixed raw materials. After melting and homogenization of the glass melt at temperatures of about 1550° C., it is poured into cold water and quenched to produce readily millable granules. The millable glass granules obtained are milled to powders having an average particle size of from 2 to 4 µm. Table 1 shows examples No. 1-3 according to the invention and a lead containing comparative glass No. 4. Table 1 also contains properties measured on these glasses, e.g. density, thermal expansion in the range from 20 to 300° C., transformation temperature ($T_g$) and the temperature at which the viscosity of the glass is $10^6$ dPas. The chemical resistance is measured by a method based on the standard DIN ISO 4794 via the decrease in mass in mg/dm$^2$ after attack by 2 mol/L of HCl for one hour at 23° C.

TABLE 1

Compositions and properties of the glasses for the frits No. 1-3 and the comparative glass No. 4:

| Glass | 1 | 2 | 3 | 4 |
|---|---|---|---|---|
| Composition (% by weight) | | | | |
| $Al_2O_3$ | 0.4 | 3.3 | 1.2 | 0.3 |
| $B_2O_3$ | 14.2 | 7.2 | 34.7 | 1.6 |
| $Bi_2O_3$ | | 64.2 | | |
| CaO | | 0.2 | | 0.1 |
| $K_2O$ | | 0.5 | | 0.1 |
| $Li_2O$ | 2.0 | 1.3 | 1.9 | 3.1 |
| MgO | | 0.1 | | 0.2 |
| $Na_2O$ | 8.6 | | | 2.5 |
| PbO | | | | 48.6 |
| $SiO_2$ | 49.2 | 21.0 | 8.9 | 41.8 |
| $TiO_2$ | 1.9 | 0.1 | | 1.7 |
| ZnO | 20.3 | 0.1 | 45.5 | |
| $ZrO_2$ | 3.4 | 2.0 | 7.8 | |
| Properties: | | | | |
| Density [g/cm$^3$] | 2.807 | 4.522 | 3.364 | 3.841 |
| Thermal expansion at from 20 to 300° C. [$10^{-6}$/K] | 7.1 | 7.3 | 5.2 | 8.7 |
| $T_g$ [° C.] | 489 | 445 | 514 | 405 |
| Temperature at which the viscosity $\eta = 10^6$ dPas [° C.] | 675 | 615 | 645 | 600 |
| Chemical resistance: 2 mol/l HCl (1 h, 23° C.) [mg/dm$^2$] | 145 | 230 | 2990 | 1 |

Glass No. 3 shows comparatively severe chemical attack, which can make it unsatisfactory for applications having demanding requirements in respect of the resistance.

The glass frits from Table 1 are processed to produce pastes or printing inks. As indicated in Table 2, the pulverulent glass frits and roughness additives are mixed in the proportions indicated and have the average particle sizes indicated. The thermal expansion of the roughness additives used is likewise indicated in Table 2.

TABLE 2

Compositions and properties of printing inks and cone coatings produced therewith; examples No. 1-5 according to the invention, comparative example No. 6

| | Example | | | | | |
|---|---|---|---|---|---|---|
| | 1 | 2 | 3 | 4 | 5 | 6 |
| Glass No. | 1 | 1 | 2 | 2 | 3 | 4 |
| Glass frit | | | | | | |
| Proportion [% by weight] | 41 | 41 | 55 | 55 | 40 | 42 |
| Particle size $d_{50}$ [µm] | 2.5 | 2.5 | 2.1 | 2.1 | 3.5 | 2.5 |
| Roughness additive | Fused $SiO_2$ | Fused $SiO_2$ | Zirconium silicate | Zirconium silicate | α-alumina | $BaSO_4$ |
| Proportion [% by weight] | 3 | 3 | 9 | 9 | 8 | 8 |
| Particle size $d_{50}$ [µm] | 1 | 1 | 1.4 | 1.4 | 1.5 | 1 |
| Thermal expansion at from 20 to 300° C. [$10^{-6}$/K] | 0.6 | 0.6 | 4.5 | 4.5 | 9 | |
| Oil addition to paste [% by weight] | 56 | 56 | 36 | 36 | 52 | 50 |
| Baking | | | | | | |
| $T_{max}$ [° C.] | 590 | 610 | 570 | 610 | 590 | 570 |
| Properties of cone coating | | | | | | |
| Average layer thickness [µm] | 4.5 | 4 | 6 | 7 | 8 | 10 |
| Roughness $R_q$ rms [µm] | 0.68 | 0.69 | 1.25 | 1.15 | 1.22 | 1.02 |
| Visual assessment | | | | | | |
| Cracks | none | none | none | none | none | a few |
| Spalling | none | none | none | none | none | none |
| Layer adhesion | + | + | + | + | + | + |
| Freedom from leaks | + | + | + | + | + | + |
| Chemical resistance | + | + | + | + | 0 | + |

+: passed without restriction
0: passed with restriction
−: not passed

The powder mixtures were processed with addition of organic oil-based pasting agents to give a paste. Various amounts of oil were added as a function of the densities of the glass frit in order to set viscosities of about 0.4 Pa·s at 35° C. Powder mixture and oil add up to 100% by weight in Table 2. To homogenize the pastes, they were treated on a three-roll mill.

Glass syringes composed of a borosilicate glass of the type FIOLAX® and having a thermal expansion of $4.9 \cdot 10^{-6}$/K in the cone region were coated with the pastes obtained. Printing of the glass cone with the pastes was carried out using a coating roller. The width of the circumferential cone coating was 5 mm. The coated glass syringes were baked in a tunnel oven at the baking temperatures indicated in Table 2 for a time of about 3 minutes. In addition, Table 2 shows the average layer thicknesses and roughness values obtained after baking. The roughness values and the layer thickness were determined by a means of a white light interferometer from Zygo.

The coatings obtained in this way are transparent to translucent and readily visible for visual monitoring for the differences in the roughness, layer thickness and geometry of the coating. The cone coatings were examined for cracks and spalling with the naked eye and under an optical microscope.

The adhesion of the coating was evaluated in a scratch test using a metal ruler. In the test, the edge of a metal ruler is scraped over the printed surface. The test is passed when no coating constituents have been scraped off. The regions tested in this way were subsequently examined under an optical microscope. The sealing/freedom from leaks was examined on sterilized (for 20 minutes at 121° C.) glass syringes. The glass syringes are closed on the cone with commercial plastic sealing caps and filled with distilled water. A pressure of 1 bar is applied in the interior and maintained for 30 seconds. To pass the test, no liquid is allowed to exit and the closure caps must not pop off.

In the measurement of the chemical resistance, the coated glass syringes were placed for 5 minutes in an acid bath of diluted hydrochloric having a pH of 2. The glass syringes were then rinsed under water and the cone coating was examined for visible changes with the naked eye and under an optical microscope. It was found that only the glass syringe as per Example 5 of Table 2 had a visually recognizable change in the cone coating. After the acid treatment, a test for freedom from leaks was again carried out. Here, there were no problems in any of the examples. It was thus found that the glass frit of Example 5 is limited in terms of its chemical resistance. The requirements for freedom from leaks were passed, but chemical attack is visibly recognizable. In applications in which a high chemical resistance is important, this type of coating should therefore not be selected.

At least ten glass syringes coated with the same material were tested in each test.

What is claimed is:

1. A syringe comprising:
   a cylinder for accommodating a liquid; and
   a cone comprising borosilicate glass having a thermal expansion in the range from 20 to 300° C. of less than $6 \cdot 10^{-6}$/K, wherein the cone encloses an outlet channel and includes an outside surface having a coating, and wherein the coating has an increased roughness compared to the outside surface and comprises a glass matrix with structure-forming particles embedded therein.

2. The syringe according to claim 1, wherein the coating has a roughness of $R_q$(rms) between 0.3 and 2 µm.

3. The syringe according to claim 1, wherein the coating has a roughness of $R_q$(rms) between 0.5 and 1.8 µm.

4. The syringe according to claim 1, wherein the coating has an average layer thickness from 0.5 to 20 µm.

5. The syringe according to claim 1, wherein the glass matrix has a viscosity of less than or equal to $10^6$ dPas below 700° C.

6. The syringe according to claim 1, wherein the structure-forming particles are ceramic or glass particles having an average particle size ($d_{50}$) from 0.2 to 5 µm.

7. The syringe according to claim 1, wherein the structure-forming particles make up a proportion of between 1 and 30% by weight of the coating.

8. The syringe according to claim 1, wherein the structure-forming particles comprise a material having a thermal expansion in the temperature range from 20 to 300° C. of less than $8 \cdot 10^{-6}$/K.

9. The syringe according to claim 8, wherein the glass matrix comprises a material having a thermal expansion of less than $7.5 \cdot 10^{-6}$/K in the temperature range from 20 to 300° C.

10. The syringe according to claim 9, wherein the glass matrix comprises a material having a thermal expansion of less than $7 \cdot 10^{-6}$/K in the temperature range from 20 to 300° C.

11. The syringe according to claim 1, wherein the glass matrix comprises a material having a thermal expansion of less than $7.5 \cdot 10^{-6}$/K in the temperature range from 20 to 300° C.

12. The syringe according to claim 11, wherein the glass matrix comprises a material having a thermal expansion of less than $7 \cdot 10^{-6}$/K in the temperature range from 20 to 300° C.

13. The syringe according to claim 1, wherein the glass matrix comprises 40 to 75% by weight of $Bi_2O_3$, 3 to 20% by weight of $B_2O_3$, and 10 to 30% by weight of $SiO_2$.

14. The syringe according to claim 1, wherein the glass matrix comprises 15 to 48% by weight of ZnO, 8 to 40% by weight of $B_2O_3$, and 8 to 52% by weight of $SiO_2$.

15. The syringe according to claim 1, wherein the coating is symmetrically disposed around the outside surface.

16. The syringe according to claim 15, wherein the coating has a width of between 2 and 10 mm.

17. The syringe according to claim 1, wherein the borosilicate glass has a thermal expansion in the range from 20° C. to 300° C. of $4.5 \cdot 10^{-6}$/K to $5.5 \cdot 10^{-6}$/K.

18. The syringe according to claim 1, wherein the borosilicate glass has a thermal expansion in the range from 20° C. to 300° C. of less than $5.0 \cdot 10^{-6}$/K.

19. The syringe according to claim 1, wherein the syringe comprises a total of less than 100 ppm of Pb, Cd, Hg and $Cr^{VI}$.

20. The syringe according to claim 1, wherein the syringe comprises a total of less than 1000 ppm of Pb, Cd, Hg and $Cr^{VI}$.

21. The syringe according to claim 1, wherein the coating does not completely cover the cone.

22. The syringe according to claim 1, wherein the outside surface of cone has the coating in a manner that provides coated areas and island-like subregions that are free of the coating.

* * * * *